(12) United States Patent
Morandi et al.

(10) Patent No.: US 11,161,805 B2
(45) Date of Patent: Nov. 2, 2021

(54) PROCESS FOR THE TRANSITION METAL CATALYZED CYANATION OF ARYL/VINYL HALIDES

(71) Applicant: STUDIENGESELLSCHAFT KOHLE MBH, Mülheim (DE)

(72) Inventors: Bill Morandi, Zürich (CH); Peng Yu, Zürich (CH)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 16/753,232

(22) PCT Filed: Oct. 2, 2018

(86) PCT No.: PCT/EP2018/076789
§ 371 (c)(1),
(2) Date: Apr. 2, 2020

(87) PCT Pub. No.: WO2019/068707
PCT Pub. Date: Apr. 11, 2019

(65) Prior Publication Data
US 2020/0325099 A1    Oct. 15, 2020

(30) Foreign Application Priority Data

Oct. 5, 2017 (DE) ................. 10 2017 123 128.5

(51) Int. Cl.
| | | |
|---|---|---|
| C07C 253/14 | (2006.01) |
| B01J 27/125 | (2006.01) |
| B01J 31/14 | (2006.01) |
| B01J 31/22 | (2006.01) |
| B01J 31/24 | (2006.01) |
| B01J 31/26 | (2006.01) |
| C07C 253/30 | (2006.01) |
| C07D 311/58 | (2006.01) |

(52) U.S. Cl.
CPC ........... *C07C 253/14* (2013.01); *B01J 27/125* (2013.01); *B01J 31/143* (2013.01); *B01J 31/2295* (2013.01); *B01J 31/2457* (2013.01); *B01J 31/26* (2013.01); *C07C 253/30* (2013.01); *C07D 311/58* (2013.01); *B01J 2231/42* (2013.01); *B01J 2531/31* (2013.01); *B01J 2531/847* (2013.01)

(58) Field of Classification Search
CPC .................................................... C07C 253/14
USPC .......................................................... 549/407
See application file for complete search history.

(56) References Cited

U.S. PATENT DOCUMENTS

2008/0194829 A1    8/2008 Muller et al.

FOREIGN PATENT DOCUMENTS

| EP | 0 613 720 A1 | 9/1994 |
| EP | 3 176 151 A1 | 6/2017 |

OTHER PUBLICATIONS

Zhang, et al."General and mild nickel-catalyzed cyanation of aryliheteroaryi chlorides with Zn(CN)2: Key Roles of DMAP"; Organic Letters 2017, 19, pp. 2118-2121.
Knemnar, et al.; "Copper catalyzed nitrile synthesis from aryl halides using formamide as a nitric source"; RSC Adv. 2014, 4, pp. 13405-13408.
Yu, et al.; "Nickel-catalyzed cyanation of aryl chlorides and triflates using butyronittile: merging retro-hydrocyanation with cross-coupling"; Angew. Chem. Int. Ed. 2017, 56, pp. 15693-15697.

*Primary Examiner* — Taofiq A Solola
(74) *Attorney, Agent, or Firm* — Norris McLaughlin, P.A.

(57) ABSTRACT

The present invention refers to a process for a transition metal, particularly nickel-catalyzed cyanation reaction of aryl/vinyl halide using organic nitrile compounds. This new reaction provides a strategically distinct approach to the safe preparation of aryl/vinyl cyanides, which are essential compounds in agrochemistry and medicinal chemistry.

8 Claims, 3 Drawing Sheets

FIG. 1: Optimization of reaction conditions

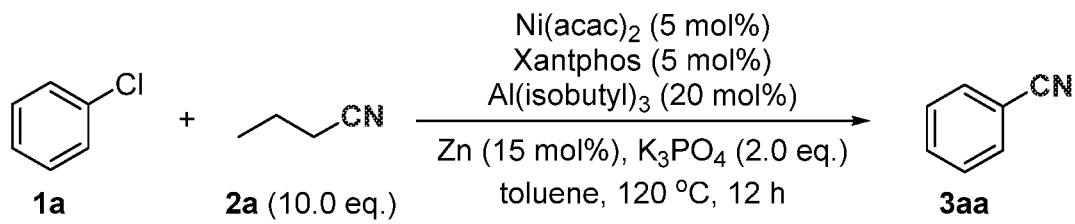

| Entry | Deviation from standard conditions | 3aa (%)[b] |
|---|---|---|
| 1 | none | 88 |
| 2 | DPEPhos instead of Xantphos | <5 |
| 3 | PPhCy$_2$ instead of Xantphos | 0 |
| 4 | NiCl$_2$·glyme instead of Ni(acac)$_2$ | 32 |
| 5 | NiBr$_2$·glyme instead of Ni(acac)$_2$ | 37 |
| 6 | Ni(COD)$_2$ instead of Ni(acac)$_2$ | 25 |
| 7 | AlMe$_2$Cl instead of Al(isobutyl)$_3$ | 27 |
| 8 | AlMe$_3$ instead of Al(isobutyl)$_3$ | 71 |
| 9 | K$_2$CO$_3$ instead of K$_3$PO$_4$ | 21 |
| 10 | Et$_3$N instead of K$_3$PO$_4$ | 59 |
| 11 | Mn instead of Zn | 27 |
| 12 | 2.0 equivalent of 2a | 22 (52[c]) |

[a] Reaction conditions: 1a (0.1 mmol), 2a (1.0 mmol), Ni(acac)$_2$ (5 mol%), Xantphos (5 mol%), Al(isobutyl)$_3$ (20 mol%), Zn (15 mol%), K$_3$PO$_4$ (2.0 eq.), toluene (0.5 mL) at 120 °C, 12 h. [b] GC yields. [c] 2a (6.0 eq.).

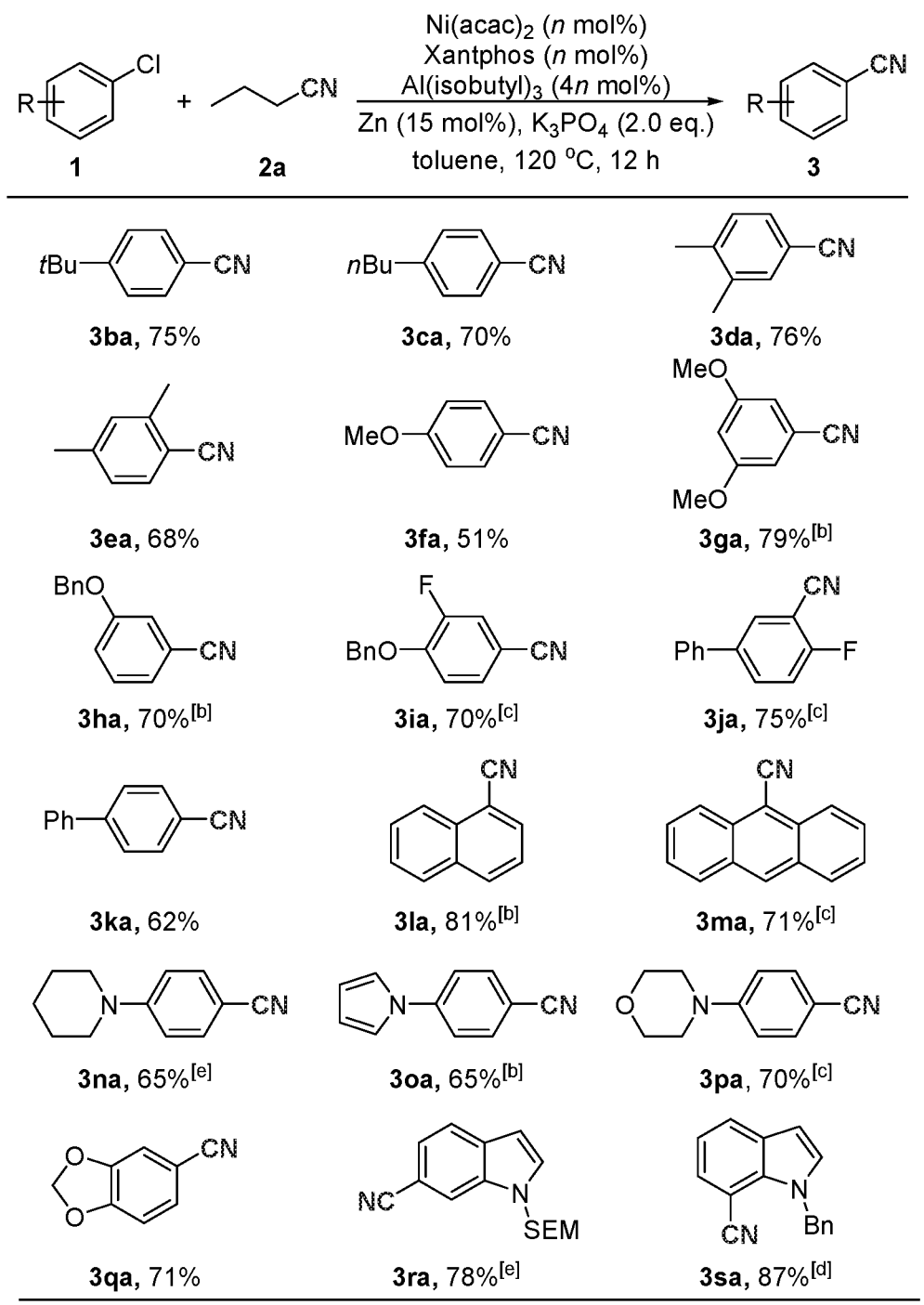
FIG. 2: Scope of nickel-catalyzed transfer cyanation of aryl chlorides.[a]
[a] Yields of isolated products. [b] n = 7.5. [c] n = 10. [d] n = 12.5. [e] n = 15.

FIG. 3: Nickel-catalyzed transfer cyanation of aryl and vinyl triflates.[a]
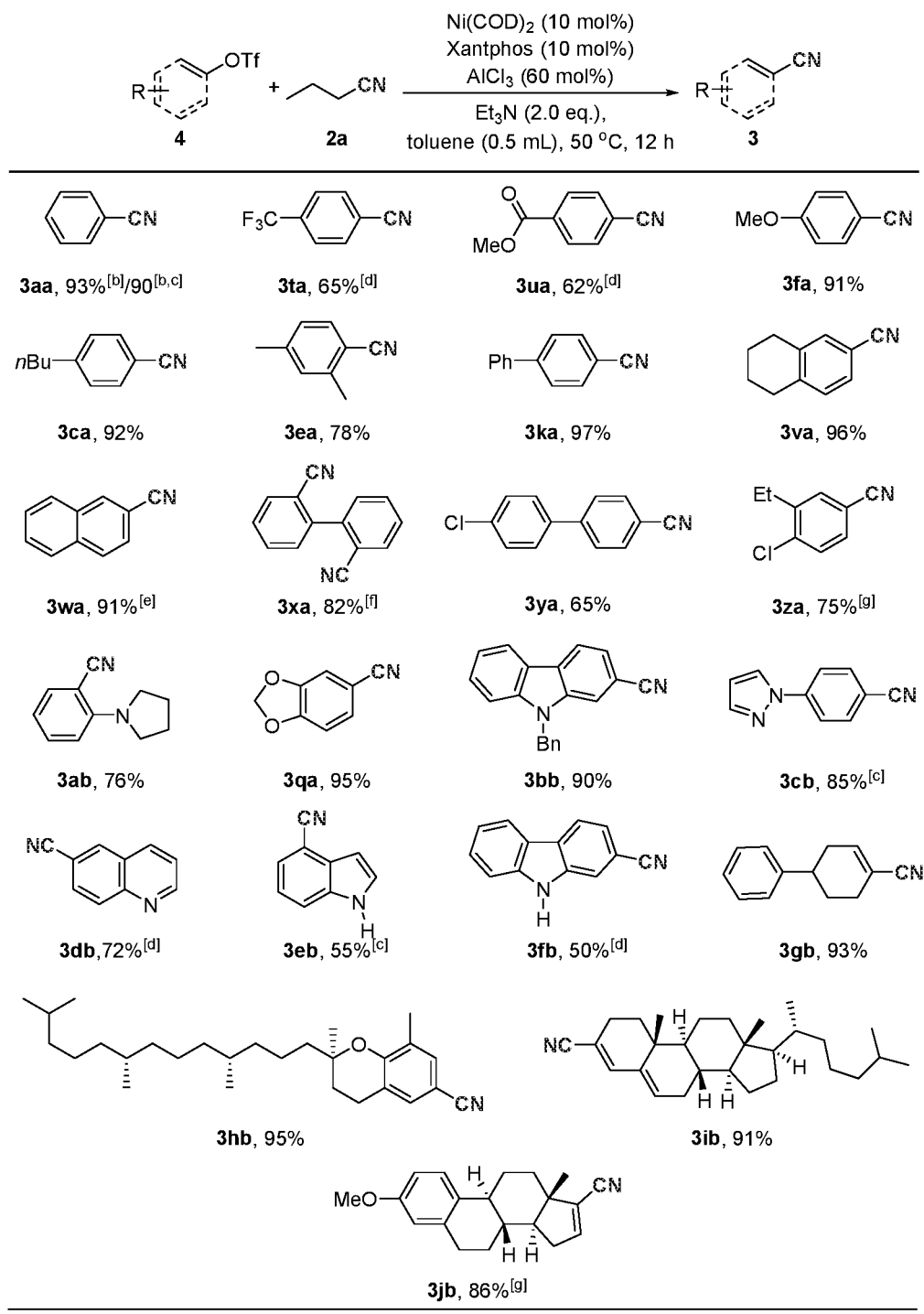
[a] Yields of isolated products. [b] GC yields. [c] 4 (0.5 mmol), 2a (1.0 mmol), toluene (1.5 mL), 50 °C, 3h, triflate added over 2h. [d] 4 (0.5 mmol), 2a (1.5 mmol), toluene (1.5 mL), 70 °C, 5h, triflate added over 4h. [e] N-Xantphos (10 mol%), 110 °C. [f] Ni(COD)2 (20 mol%), Xantphos (20 mol%), AlCl3 (120 mol%), Et3N (4.0 eq.). [g] 80 °C

PROCESS FOR THE TRANSITION METAL CATALYZED CYANATION OF ARYL/VINYL HALIDES

This application is a 371 of PCT/EP2018/076789, filed Oct. 2, 2018, which claims foreign priority benefit under 35 U.S.C. § 119 of German Patent Application No. 10 2017 123 128.5, filed Oct. 5, 2017, the disclosures of which are incorporated herein by reference.

The present invention refers to a process for a transition metal, particularly nickel-catalyzed cyanation reaction of aryl/vinyl halides. This new reaction provides a strategically distinct approach to the safe preparation of aryl/vinyl cyanides, which are essential compounds in agrochemistry and medicinal chemistry.

Aromatic nitriles are found in a wide range of pharmaceuticals, agrochemicals, natural products and organic materials. Moreover, aryl nitriles are among the most versatile synthetic intermediates because they can be readily converted to aldehydes, carboxylic acids, ketones, amides, amines, and heterocycles. The development of efficient and practical routes for the synthesis of aryl nitriles has thus been a longstanding goal of organic synthesis.

To bypass the limitations of the venerable Sandmeyer and Rosenmund-von Braun reaction that employ stoichiometric amounts of CuCN, the transition-metal catalyzed cyanation of aryl halides has been introduced. While the use of earth-abundant metals as catalysts and less reactive aryl halides as substrates remains challenging, the most severe drawback of the vast majority of the current protocols continues to be the reliance upon highly toxic cyanide salts as reagents.

Traditionally, metal cyanide salts (KCN, NaCN, Zn(CN)$_2$, TMSCN or acetone cyanohydrin have been used in the transition-metal-catalyzed cyanation of aryl halides (Scheme 1). The common feature among all these reagents is the relative ease by which the cyano group can be transferred to the metal catalyst, ensuring a facile cyanation reaction. However, this feature is also often responsible for catalyst deactivation through formation of inactive catalytic species bearing multiple cyanide ligands. More importantly, the facile release of the cyanide anion is responsible for the high toxicity of these reagents, which generates significant safety concerns for both academic and industrial applications.

To address these safety concerns, K$_4$[Fe(CN)$_6$], a non-toxic food additive, has been introduced as a reagent for the cyanation of aryl halides by the Beller and Weissman group. However, the low solubility of this reagent in organic solvents and its low rate of transmetallation has limited its broader application, in part because of scalability issues due to the heterogeneous nature of the reaction mixture. Additionally, the use of this reagent leads to the formation of metal wastes. Thus, the development of novel, non-toxic reagents addressing these challenges remains of great significance.

Consequently, the inventors designed a method employing simple, non-hydrolysable alkyl nitriles as benign cyanating reagents, thus providing a complementary tool for the safe preparation of aryl and vinyl cyanides.

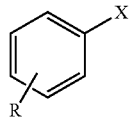

The inventors considered that the installation of a cyano group through transition-metal catalyzed activation of C—CN bonds enables the use of inexpensive and less toxic alkyl nitriles as reagents. This strategy provides a controlled way to generate metal-cyanide intermediates without employing metal cyanide sources, avoiding both catalyst deactivation and exposure to toxic reagents.

The inventors considered that simple alkyl nitriles bearing β-hydrogens could be employed as cyanating reagents in transition-metal-catalyzed cyanation of aryl (pseudo)halides (Scheme 2).

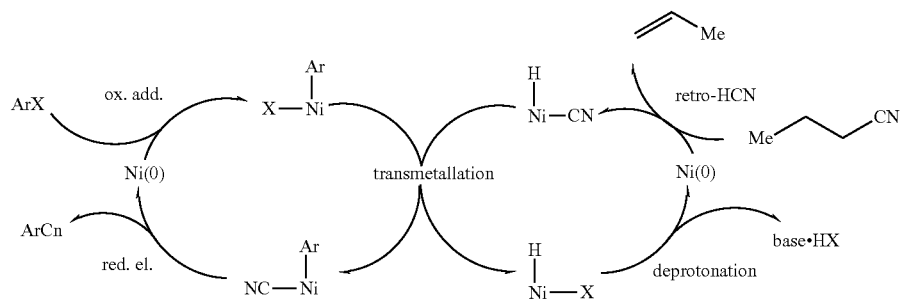

With regard to the mechanism, the inventors envisaged that a transmetallation event between two independently generated catalytic intermediates, H—Ni—CN (generated through oxidative addition of the C—CN bond followed by β-hydride elimination) and Ar—Ni—X (generated through oxidative addition of Ar—X), leads to the formation of the desired aryl cyanide after reductive elimination. Reaction of H—Ni—X with a base could then regenerate the catalytically active Ni(0) species (Scheme 2).

Thus, the present invention is directed to a process for conversion of a aryl/vinyl halide/triflate (I) into an aryl/vinyl nitrile (III) using an alkylnitrile (II) as reagent in the presence of a transition metal coordinated to a ligand and a Lewis acid co-catalyst, and a base, preferably in a solvent:

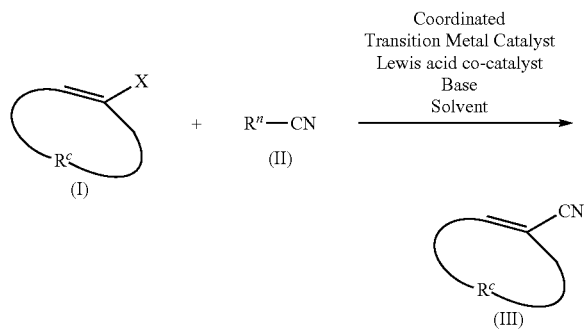

Wherein:
R$^c$ represents a C$_3$ to C$_6$ hydrocarbon chain which forms a five to eight-membered optionally substituted hydrocarbon ring system with the vinyl moiety;
X represents halogen or triflate,
R$^n$ represents a straight chain C$_3$ to C$_{12}$ alkyl group;
the metal of the coordinated transition metal catalyst is selected from a metal of the Iron-group, Cobalt-group, Nickel-group or Copper group;
the ligand of the coordinated transition metal catalyst is selected from compounds having the ability to coordinate to said transition metal, including phosphorous-, nitrogen-, As-, Sb- or N-heterocyclic based ligands;
the Lewis acid co-catalyst is selected from compounds of aluminum, boron, zinc, titanium, scandium, and
the base is selected from common inorganic or organic bases having a moderate basicity (5<pKa conjugated acid <35), such as K$_3$PO$_4$, Et$_3$N, EtiPr$_2$N, K$_2$CO$_3$, Cs$_2$CO$_3$, NaOtBu, KOtBu, NaOH, KOH.

In one embodiment, R$^c$ represents a C$_3$ to C$_6$ hydrocarbon chain which forms a five to eight-membered optionally substituted hydrocarbon ring system with the vinyl moiety which ring system may be a cycloalkyl, heterocycloalkyl, aryl, aralkyl, heteroaryl or heteroaralkyl hydrocarbon, which may be part of a hydrocarbon ring system having up to 30, preferably up to 20 carbon atoms and which may optionally be substituted by one or more groups selected from alkyl, cycloalkyl, heterocycloalkyl, alkenyl, alkynyl, aryl, aralkyl, heteroaryl, heteroaralkyl or a heterosubstituent.

In a further embodiment, R$^c$ represents a C$_3$ to C$_4$ hydrocarbon chain which forms a five to six membered optionally substituted aromatic or heteroaromatic hydrocarbon ring system with the vinyl moiety, which may be part of a hydrocarbon ring system having up to 30, preferably up to 20 carbon atoms and which may optionally be substituted by one or more groups selected from alkyl, cycloalkyl, heterocycloalkyl, alkenyl, alkynyl, aryl, aralkyl, heteroaryl, heteroaralkyl or a heterosubstituent.

The inventors have evaluated a range of metals for use as coordinated metal catalysts to develop the transfer cyanation reaction. Amongst the transition metal catalysts, transition metals and compounds thereof, selected from the Iron-group, Cobalt-group, Nickel-group or Copper group, the groups 8 to 11 of the periodic table, particularly Nickel, Cobalt and Palladium, more particularly Nickel, are preferred. Examples are Ni(COD)$_2$, Ni(acac)$_2$, Ni(CO)$_4$, Pd(dba)$_2$, Pd(OAc)$_2$, Co$_2$(CO)$_8$ and preferred examples are Ni(acac)$_2$ or Ni(COD)$_2$.

Nickel was chosen as a metal because Nickel(0) complexes have been shown to be the active species in the oxidative addition of inert bonds, including aliphatic C—CN bonds. However, initial experiments using simple Nickel catalysts alone failed to afford any product formation. Since Lewis Acids can both accelerate some Nickel-mediated reactions, the inventors made use of the addition of a Lewis Acid co-catalyst for facilitating the desired transfer cyanation mechanism.

The inventors also evaluated a range of ligands to increase the activity of the coordinated metal catalyst in the transfer cyanation reaction. The ligand can be selected from compounds having the ability to coordinate to a transition metal, including phosphorous-, nitrogen-, As-, Sb- or N-heterocyclic based ligands. Examples are from the group consisting of phosphine ligands, particularly PPh$_3$, PCy$_3$, P(OPh)$_3$, PEt$_3$, BINAP, Xanthphos, DuPhos, DPEPhos, dppf, dppe, further preferred Xanthphos, and mixtures thereof. Preferred examples are phosphine ligands, examples of which are Xanthphos, or mixtures thereof with the following meanings:
BINAP: 2,2'-Bis(diphenylphosphino)-1,1'-binaphthalene
Xanthphos: 4,5-Bis(diphenylphosphino)-9,9-dimethylxanthene
DuPhos: (−)-1,2-Bis-2,5-diethylpholano) benzene
DPEPhos: (Oxydi-2,1-phenylene)bis(diphenylphosphine)
dppf: 1,1'-Ferrocenediyl-bis(diphenylphosphine)
dppe: 1,2-Bis(diphenylphosphino)ethane The coordinated transition metal catalyst can be prepared in situ by addition of said ligands to a solution of the transition metal compound, said metal being selected from the Iron-group, Cobalt-group, Nickel-group or Copper group, the groups 8 to 11 of the periodic table, whereby coordinated transition metal catalysts with the metal Nickel, Cobalt or Palladium are preferred. Examples of such compounds to be added are Ni(COD)$_2$, Ni(acac)$_2$, Ni(CO)$_4$, Pd(dba)$_2$, Pd(OAc)$_2$, Co$_2$(CO)$_6$ and preferred examples are Ni(COD)$_2$ and Ni(acac)$_2$.

The Lewis acid co-catalyst can be any known Lewis acid catalyst having sufficient Lewis acid strength and can be selected from compounds of aluminum, boron, zinc, titanium, scandium. Examples are Al(alkyl)$_{3-z}$Xz, wherein alkyl is C$_1$ to C$_6$, Z is 0 to 3 and X is halogen, preferred chlorine, such as AlMe$_3$, AlMe$_2$Cl, AlMeCl$_2$, AlCl$_3$, BPh$_3$, B(C$_6$F$_5$)$_3$, Zn(OTf)$_2$, ZnCl$_2$, TiCl$_4$, Sc(OTf)$_3$, and preferred examples are AlMe$_3$, Al(isobutyl)$_3$, AlMe$_2$Cl, AlCl$_3$, BPh$_3$.

The solvent is not critical and can be selected amongst those which are commonly used for such kind of catalysed reactions, such as aromatic solvents such as toluene, benzene, xylene, cymene, chlorobenzene, dichlorobenzene, or aliphatic hydrocarbon solvents, depending on the specific reaction system.

The reaction temperature is usually in the range from 25 to 150° C., preferably from 25 to 125° C.

Definition for the substituents as used in the present formulae are given in the following.

A heterosubstituent according to the invention is to be understood as a substituent including heteroatoms, preferentially selected from O, N, S, Si and halogens. It can be preferentially selected from, =O, —OH, —F, —Cl, —Br, —I, —CN, —N$_3$, —NO$_2$, —SO$_3$H, NCO, NCS, OP(O)(OR$^{S1}$)(OR$^{S2}$), OP(OR$^{S1}$)(OR$^{S2}$), a monohalogenomethyl group, a dihalogenomethyl group, a trihalogenomethyl group, —CF(CF$_3$)$_2$, —SF$_5$, —NR$^{S1}$$_2$, —OR$^{S1}$, —OOR$^{S1}$, —OSiR$^{S1}$R$^{S2}$R$^{S3}$, —OSi(OR$^{S1}$)R$^{S2}$R$^{S3}$, —OSi(OR$^{S1}$)(OR$^{S2}$)R$^{S3}$, —OSi(OR$^{S1}$)(OR$^{S2}$)(OR$^{S3}$), —OSO$_2$R$^{S1}$, —SR$^{S1}$, —SSR$^{S1}$, —S(O)R$^{S1}$, —S(O)$_2$R$^{S1}$, —C(O)OR$^{S1}$, —C(O)NR$^{S1}$R$^{S2}$, —NR$^{S1}$C(O)R$^{S2}$, —C(O)—R$^{S1}$, —COOM, wherein M may be a metal such as Na, K or Cs.

R$^{S1}$ R$^{S2}$ and R$^{S3}$ each individually represent H, alkyl, cycloalkyl, heterocycloalkyl, aryl, heteroaryl, aralkyl, heteroaralkyl, sulfonyl, silyl, each being optionally substituted by one or more alkyl, cycloalkyl, heterocycloalkyl, heteroaryl, aralkyl, heteroaralkyl, sulfonyl or heterosubstituent.

For the reaction system in more detail, alkyl may be C$_1$-C$_{20}$-Alkyl which can be straight chain or branched or cyclic and has 1, 2, 3, 4, 5, 6, 7, 8, 9, 10, 11, 12, 13, 14, 15, 16, 17, 18, 19 or 20 carbon atoms. Alkyl might particularly be C$_1$-C$_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

Cycloalkyl may be a cyclic alkyl group forming a 3 to 20 membered ring and might be cyclopropyl, cyclobutyl, cyclopentyl, cyclohexyl, cycloheptyl or cyclooctyl.

Heterocycloalkyl may be a cycloalkyl forming a 3 to 10 membered ring and incorporating one or more heteroatoms selected from N, O and S within the cycle. In particular, heterocycloalkyls can be preferentially selected from 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Halogen is F, Cl, Br or I.

Aryl might be phenyl, naphthyl or biphenyl and substituted derivatives thereof.

Aralkyl might be benzyl, naphthylmethyl and substituted derivatives thereof.

Heteroaryl may have one or more heteroatoms selected from N, O, S and Si and is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benz-imidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

Heteroaralkyl might be any of the aforementioned heteroaryl bound to an alkyl group, such as pyridinylmethyl.

Optionally substituted means unsubstituted or monosubstituted, disubstituted, trisubstituted, tetrasubstituted, pentasubstituted, or even further substituted on the respective group.

Thus, the inventors have shown that a reaction pair of a coordinated transition metal catalyst, a Lewis acid co-catalyst and a base can be used for a nitrile transfer from a hydrocarbon nitrile to replace halogen/triflate of an unsaturated halide/triflate hydrocarbon, wherein
the metal of the coordinated transition metal catalyst is selected from a metal of the Iron-group, Cobalt-group, Nickel-group or Copper group;
the ligand of the coordinated transition metal catalyst is selected from compounds having the ability to coordinate to said transition metal, including phosphorous-, nitrogen-, As-, Sb- or N-heterocyclic based ligands; and
the Lewis acid co-catalyst is selected from compounds of aluminum, boron, zinc, titanium, scandium,
the base is selected from common inorganic or organic bases having a moderate basicity (5<pKa conjugated acid <35), such as K$_3$PO$_4$, Et$_3$N, EtiPr$_2$N, K$_2$CO$_3$, Cs$_2$CO$_3$, NaOtBu, KOtBu, NaOH, KOH,
so that aromatic/vinyl nitrile compounds are accessible without the need of using toxic inorganic cyanide salts.

The invention is further illustrated in the attached drawings and the following experimental section below.

In the attached drawings:

FIG. 1 illustrates options for the optimization of reaction conditions;

FIG. 2 illustrates the scope of nickel-catalyzed transfer cyanation of aryl chlorides; and FIG. 3 illustrates Nickel-catalyzed transfer cyanation of aryl and vinyl triflates.

EXPERIMENTAL PART

To test their hypothesis, the inventors selected butyronitrile 2a as an inexpensive reagent (~80€/L) to cyanate aryl chloride 1a (Table 1). The choice of 2a as cyanating agent is accounted for its low price, low-molecular weight and high volatility of the corresponding alkene by-product. After careful evaluation of reaction parameters, the inventors found that a combination of inexpensive and bench-stable Ni(acac)$_2$, Xantphos, Al(isobutyl)$_3$ as co-catalyst, Zn as reducing agent to generate Ni(0) and K$_3$PO$_4$ as base in toluene at 120° C. gave the best result within 12 hours, delivering 3aa in 88% GC yield (entry 1). It is noteworthy that undesired homodimerization or Heck-type reactions were not observed under the reaction conditions. The results of ligand optimization showed that the use of a bidentate ligand with a smaller bite angle hampered the reactivity of this cyanation reaction, and no product was detected when the reaction was treated with a monodentate phosphine ligand (entries 2 and 3). As shown in entries 4-8, the use of other precatalysts or co-catalysts resulted either in lower yields of 3aa or no product formation, indicating that an aluminium Lewis acid plays a critical role in the activation of the C—CN bond. Likewise, other bases or reducing agent had a deleterious effect on the outcome of the reaction (entries 9-11). Lower yields of 3*aa* were obtained when the reaction was treated with fewer equivalents of 2a (entry 12), probably reflecting the slower rate of retro-hydrocyanation relative to the oxidative addition of the aryl chloride.

With optimized conditions in hand, the inventors examined the substrate scope of this nickel-catalyzed transfer cyanation of aryl chlorides. As shown in table 2 illustrating the scope of nickel-catalyzed transfer cyanation of aryl chlorides, substrates bearing electron donating or withdrawing substituents, whether they were at the para, meta or even ortho position, reacted well under our optimized reaction conditions (3ba-3ja), revealing a good tolerance to steric and electronic effects. Naphthyl and 9-phenanthryl chlorides can also be converted to the corresponding aryl nitriles in good yields (3la, 3ma). Several nitrogen and oxygen heterocycles relevant to the drug discovery process, such as pyrrole, morpholine, dioxole and indole, could be efficiently tolerated by the catalytic system (3oa-3sa).

To demonstrate the robustness and generality of the inventive method, the inventors extended the scope to aryl and vinyl triflates as another important class of electrophiles. Despite the fact that triflate electrophiles, which can be easily accessed from phenols or aliphatic ketones, are retrosynthetically complementary to halides, they have not been frequently used in transition-metal catalyzed cyanation reactions. In particular, few examples of nickel-catalyzed cyanation of aryl triflates have been reported, and these protocols all rely on highly toxic KCN as cyanating reagent.

After a slight modification of the reaction conditions, the inventors found that several aryl and vinyl triflates can be successfully converted to the corresponding cyano products in good to excellent yields (62-97%) under mild reaction conditions (Ni(cod)$_2$, Xantphos, AlCl$_3$, Et$_3$N in toluene at 50-110° C. for 3-12 hours).

As shown in Table 3, substrates bearing either electron deficient (3ta, 3ua) or electron donating groups (3fa, 3ca, 3ea, 3va) can be efficiently converted to aryl nitriles in excellent yields. Ortho substituted substrates reacted well under our reaction conditions, even though slightly lower yields were obtained (3ea, 3xa).

A chemoselective reaction of the triflate electrophile could be realized in the presence of a chloride, furnishing the desired products in good yields (3ya, 3za). Heterocycles such as pyrrolidine, dioxole, carbazole, pyrazole and quinoline were well tolerated under our conditions (3ab, 3qa, 3bb, 3cb, 3db). Even unprotected indole and carbazole substrates could be well tolerated (3eb, 3fb). Interestingly, vinyl triflates efficiently afforded synthetically versatile vinyl nitriles in excellent yields (3gb). To further demonstrate the diversity and practicability of this developed method, a few natural products, such as 5-tocopherol, cholesterol and estrone, were transformed into the corresponding triflates before being subjected to the transfer cyanation conditions to obtain excellent yields of the desired products (3hb-3jb).

Notably, the amount of the reagent can be reduced from 10 equiv. to 2 equiv. when the electrophile is slowly added to the reaction mixture (3aa).

The method could also be employed on a preparative scale when the reaction was performed in an open system to facilitate the rapid release of the propene side-product (Scheme 2).

Scheme 2. Gram scale experiment.

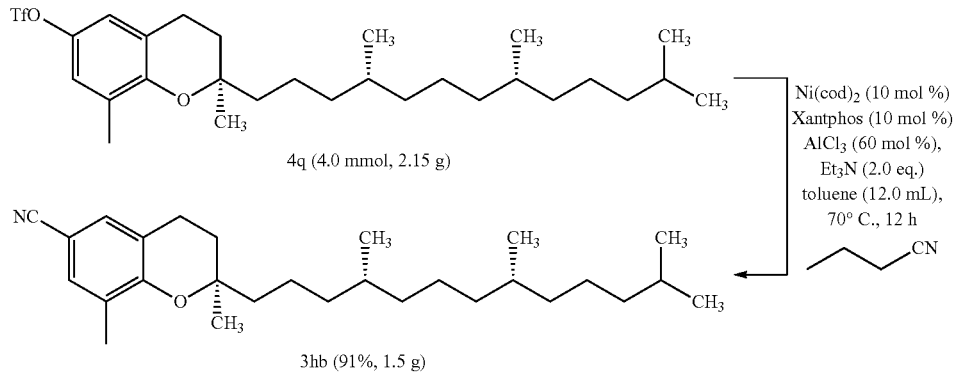

Several control reactions were then performed to gather preliminary information about the mechanism. The inventors demonstrated the occurrence of the proposed retro-hydrocyanation step through the detection of undecene isomers resulting from the retro-hydrocyanation of dodecanitrile (Scheme 3, eq. 1).

The inventors also explored whether retro-hydrocyanation proceeds in the absence of electrophile. In this experiment, only small amounts of alkene isomers were observed, showing that retro-hydrocyanation cannot be performed efficiently in the absence of the electrophile. The normal reaction course resumed after addition of the electrophile, further suggesting that a direct transfer of the cyanide anion between two nickel(II)-species is the main pathway of the reaction (Scheme 3, eq. 2). Additional control experiments using a simple ammonium cyanide salt or acetone cyanohydrin as reagents did not give any conversion, further suggesting that our reaction is not proceeding through the in situ generation of an ammonium cyanide reagent (Scheme 3, eq. 3 and 4). Taken altogether, these experiments are best explained by a double catalytic cycle as presented in Scheme 2. Within this mechanistic context, the ability to drastically decrease the amount of butyronitrile reagent when the electrophile is slowly added to the reaction mixture (vide supra) highlights the critical importance of matching the rate of retro-hydrocyanation with that of aryl (pseudo)halide oxidative addition.

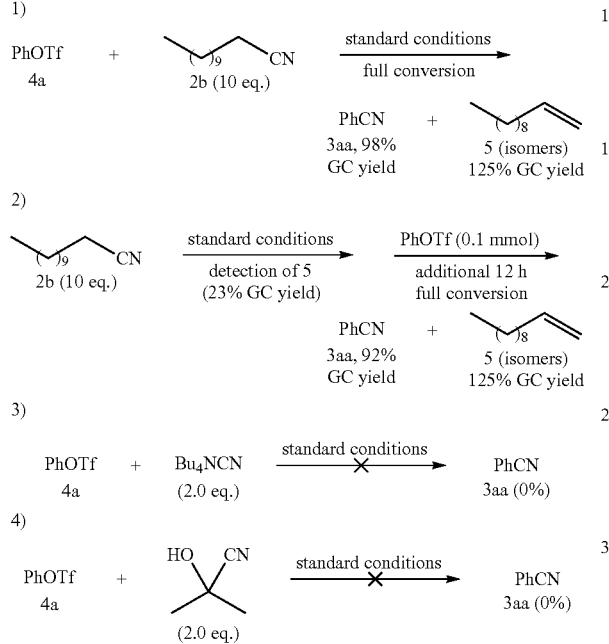

General Procedure for the Cyanation of Aryl Chlorides

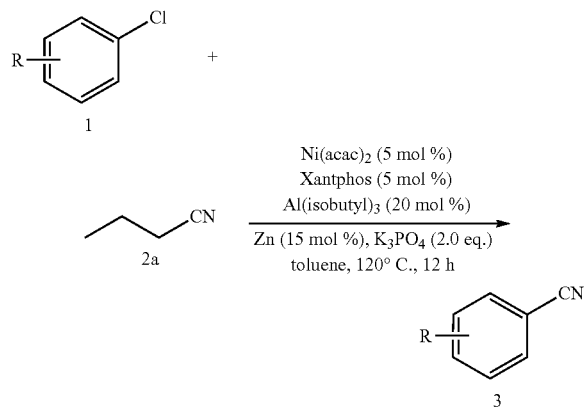

Under argon, to an 8.0 mL Screw-cap vial equipped with a magnetic stirring bar was added Ni(acac)$_2$ (2.6 mg, 5 mol %), Xantphos (5.8 mg, 5 mol %), Zn (2.0 mg, 15 mol %) and toluene (0.5 mL). The mixture was allowed to stir for 5 min. Then butyronitrile (138.2 mg, 2.0 mmol), aryl chloride (0.2 mmol), K$_3$PO$_4$ (84.9 mg, 0.4 mmol) and Al(isobutyl)$_3$ (25% in toluene, 31.7 mg, 20 mol %) were added sequentially to the resulting solution and the vial was sealed and placed on a heating plate (120° C.). After stirring for 12 hours, the reaction mixture was cooled to room temperature and quenched by adding two drops of water. The reaction mixture was dried over anhydrous Na$_2$SO$_4$ and concentrated under reduced pressure. Products were obtained after purification by flash column chromatography on silica gel. The scope of the obtainable products is illustrated in FIG. 2.

General Procedure for the Cyanation of Aryl Triflates

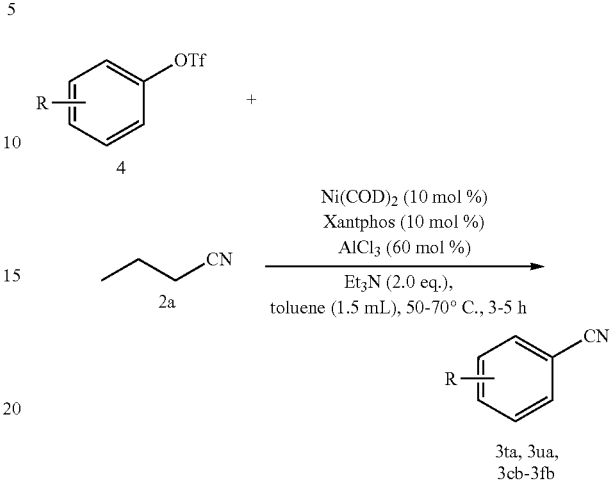

Under argon, to an 16.0 mL Screw-cap vial equipped with a magnetic stirring bar was added Ni(COD)$_2$ (13.8 mg, 10 mol %), Xantphos (29.2 mg, 10 mol %) and toluene (0.5 mL). The mixture was allowed to stir for 5 min. Then butyronitrile (103.7 mg, 1.0 mmol), Et$_3$N (139.0 µL, 1.0 mmol) and AlCl$_3$ (40.0 mg, 60 mol %) were added sequentially to the resulting solution and the vial was sealed and placed to a heating plate (70° C.). Then a solution of aryl triflates (0.5 mmol) in toluene (1.5 mL) was slowly dosed into the stirring reaction mixture via syringe pump during 2-4 hours. Alternatively, the aryl triflate can in some cases also be directly added to the reaction mixture all at once. After an additional stirring for 1 hour at 50-70° C., the reaction mixture was cooled to room temperature and quenched by adding a few drops of water. The reaction mixture was dried over anhydrous Na$_2$SO$_4$ and concentrated under reduced pressure. Products were obtained after purification by flash column chromatography on silica gel. The scope of the obtainable products is illustrated in FIG. 3.

In conclusion, a new transition metal, in particular nickel-catalyzed cyanation reaction has been developed, enabling the conversion of a broad range of aryl chlorides and aryl/vinyl triflates into aryl/vinyl nitriles using benign butyronitrile as reagent. The use of nontoxic and inexpensive butyronitrile as a cyanating agent not only addresses the safety issues encountered with most of the current cyanation reactions, but also overcomes other drawbacks by preventing catalyst deactivation and ensuring homogeneity of the reaction mixture. In a broader context, the inventors are convinced that the new concept delineated in this work, namely the merger of transfer functionalization and cross-coupling, will open new avenues in synthetic organic chemistry.

The invention claimed is:
1. A process comprising converting an aryl/vinyl halide/triflate (I) into an aryl/vinyl nitrile (III) using an alkylnitrile (II) as reagent in the presence of a transition metal coordinated to a ligand and a Lewis acid co-catalyst, and a base, optionally in a solvent, as represented in the following scheme:

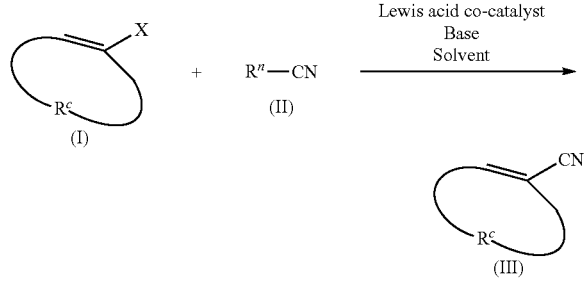

Wherein:
R$^c$ represents a C$_3$ to C$_6$ hydrocarbon chain which forms a five to eight-membered optionally substituted hydrocarbon ring system with the vinyl moiety;
X represents halogen or triflate,
R″ represents a C$_3$ to C$_{12}$ alkyl group;
the coordinated transition metal catalyst comprises a metal selected from a metal of the Iron-group, Cobalt-group, Nickel-group or Copper group;
the ligand is selected from compounds having the ability to coordinate to said transition metal;
the Lewis acid co-catalyst is selected from compounds of aluminum, boron, zinc, titanium, scandium, and
the base is selected from common inorganic or organic bases having 5<pKa conjugated acid <35.

2. Process according to claim 1 wherein R$^c$ represents a C$_3$ to C$_6$ hydrocarbon chain which forms a five to eight-membered optionally substituted hydrocarbon ring system with the vinyl moiety which ring system may be a cycloalkyl, heterocycloalkyl, aryl, aralkyl, heteroaryl or heteroaralkyl hydrocarbon, which may be part of a hydrocarbon ring system having up to 30 carbon atoms and which may optionally be substituted by one or more groups selected from alkyl, cycloalkyl, heterocycloalkyl, alkenyl, alkynyl, aryl, aralkyl, heteroaryl, heteroaralkyl or a heterosubstituent.

3. Process according to claim 1 wherein R$^c$ represents a C$_3$ to C$_4$ hydrocarbon chain which forms a five to six membered optionally substituted aromatic or heteroaromatic hydrocarbon ring system with the vinyl moiety, which may be part of a hydrocarbon ring system having up to 30 carbon atoms and which may optionally be substituted by one or more groups selected from alkyl, cycloalkyl, heterocycloalkyl, alkenyl, alkynyl, aryl, aralkyl, heteroaryl, heteroaralkyl or a heterosubstituent.

4. Process according to claim 1 wherein R″ is a R″ represents a straight chain C$_6$ to C$_9$ alkyl group.

5. Process according to claim 1, wherein the coordinated transition metal catalyst is obtained from a transition metal catalyst precursor selected from Ni(COD)$_2$, Ni(acac)$_2$, Ni(CO)$_4$, Pd(dba)$_2$, Pd(OAc)$_2$, Co$_2$(CO)$_8$.

6. Process according to claim 1 wherein the ligand of the coordinated transition metal catalyst is selected from compounds having the ability to coordinate to said transition metal selected from phosphorous-, nitrogen-, As-, Sb- or N-heterocyclic based ligands.

7. Process according to claim 1, wherein the ligand is selected from the group consisting of phosphine ligands, particularly PPh$_3$, PCy$_3$, P(OPh)$_3$, PEt$_3$, BINAP, Xanthphos, DuPhos, DPEPhos, dppf, dppe, and mixtures thereof.

8. Process according to claim 1, wherein the Lewis acid co-catalyst is selected from AlMe$_3$, Al(isobutyl)$_3$, AlMe$_2$Cl, AlMeCl$_2$, AlCl$_3$, BPh$_3$, B(C$_6$F$_5$)$_3$, Zn(OTf)$_2$, ZnCl$_2$, TiCl$_4$, Sc(OTf)$_3$.

* * * * *